_United States Patent_ [19]

Ruopp et al.

[11] 4,264,526
[45] Apr. 28, 1981

[54] BORATE REDUCTION OF NITROPHENOLS

[75] Inventors: Donald C. Ruopp, Belleville, N.J.;
Mark A. Thorn, Yonkers, N.Y.

[73] Assignee: Penick Corporation, Lynhurst, N.J.

[21] Appl. No.: 54,388

[22] Filed: Jul. 2, 1979

[51] Int. Cl.³ .................... C07C 103/32; C07C 89/00; C07C 85/11
[52] U.S. Cl. .................... 564/223; 564/418; 564/443
[58] Field of Search .................... 260/575, 562 A

[56] References Cited

U.S. PATENT DOCUMENTS

| | | | |
|---|---|---|---|
| 2,799,692 | 7/1957 | Croxall et al. | 260/562 A X |
| 2,945,870 | 7/1960 | Young | 260/562 A X |
| 3,042,719 | 7/1962 | Hahn et al. | 260/562 A |
| 3,076,030 | 1/1963 | Freifelder | 260/562 A |
| 3,177,256 | 4/1965 | Holtzclaw et al. | 260/575 |

OTHER PUBLICATIONS

Wertheim, "Organic Chemistry", 3rd Edition, pp. 490–491, (1954).

_Primary Examiner_—John Doll
_Attorney, Agent, or Firm_—David H. LeRoy

[57] ABSTRACT

A process for the direct production of aminophenol and N-acetyl-p-aminophenol from nitrophenols using a borate ion additive during hydrogenation to eliminate undesirable by-products and color formation.

21 Claims, No Drawings

BORATE REDUCTION OF NITROPHENOLS

FIELD OF INVENTION

This invention relates to the production of aminophenols and N-acetyl-p-aminophenol.

BACKGROUND OF INVENTION

Aminophenols are generally known to be useful as dye intermediates, particularly for the so-called azo and sulfur dyes. Aminophenols are intermediates for pharmaceuticals, such as for amino salicyclic acid or APAP. In addition, aminophenols are used as oil additives, as photographic developers and as antioxidants.

N-acetyl-p-aminophenol (APAP) is a known compound widely used as an analgesic and anti-pyretic agent in various therapeutic preparations. A commercial method for preparing N-acetyl-p-aminophenol involves reduction of p-nitrophenol to p-aminophenol and then acetylation wherein the p-aminophenol is dispersed in a non-aqueous solvent and/or excess anhydride.

The conventional process for the reduction of p-nitrophenol to produce p-aminophenol involves catalytically hydrogenating the p-nitrophenol in the presence of strong acids such as sulfuric, hydrochloric and phosphoric acids as shown in U.S. Pat. No. 2,198,249. Other acids such as oxalic or sulfonic acids as disclosed in U.S. Pat. No. 2,525,515 have also been used. Metal catalysts used for reduction include aluminum as in U.S. Pat. No. 2,525,515; platinum, palladium or noble metal catalysts and their oxides as described in U.S. Pat. Nos. 2,947,781; 3,076,030; 3,079,435; 3,328,465; 3,383,416; 3,654,365 and 3,383,416; and molybdenum sulfide or platinum sulfide-on-carbon as in U.S. Pat. No. 3,953,309.

In all of these methods, the p-aminphenol which is obtained is relatively impure and requires substantial purification before it can be further used in the production of APAP. Unfortunately, by-products are formed in the reduction of the p-nitrophenol and in the acetylation which lead to off-color and impure APAP thus requiring further purification and crystallization steps to produce an acceptable product as described in U.S. Pat. Nos. 3,658,905; 3,694,508; 3,703,598; 3,717,680; 3,845,129; 3,876,703 and 3,953,283.

Attempts to overcome the discoloration and by-product formation by various techniques have not been entirely successful or economical. The use of a reducing atmosphere and non-oxidizing acids is described in U.S. Pat. Nos. 3,177,250; 3,042,719 and 3,223,727. More recently simultaneous reduction of p-nitrophenol and acetylation of the p-aminophenol product while using an acetic acid solvent or acetic anhydride solvent system without prior isolation of the p-aminophenol has been reported as in U.S. Pat. Nos. 3,076,030 and 3,341,587.

The principle method for the preparation of p-nitrophenol begins with nitration and chlorination of benzene to produce p-chloronitrobenzene. The p-chloronitrobenzene then is subjected to alkaline hydrolysis to produce the p-nitrophenol. The p-nitrophenol must be purified and separated from the hydrolysate before it can be used to prepare acceptable APAP according to the conventional processes. Heretofore in the preparation of N-acetyl-p-aminophenol (APAP) it has been necessary to follow expensive and laborious purification procedures for p-nitrophenol, p-aminophenol and the APAP to insure an acceptably pure APAP product for therapeutic preparations.

SUMMARY OF THE INVENTION

In accordance with this invention, a process is provided for the production of aminophenol which comprises the steps of hydrolysing halonitrobenzene to form a hydrolysate product containing the corresponding nitrophenol, hydrogenating the hydrolysate product in the presence of borate ion to convert the nitrophenol to aminophenol and recovering the aminophenol.

In another embodiment, the present invention is directed to a process for the production of N-acetyl-p-aminophenol which comprises the steps of hydrolysing p-chloronitrobenzene to form a hydrolysate product containing p-nitrophenol, hydrogenating the hydrolysate product in the presence of borate ion to convert said p-nitrophenol to p-aminophenol, treating the p-aminophenol with acetic anhydride to affect acetylation of said p-aminophenol and recovering the N-acetyl-p-aminophenol from the final reaction product.

It has unexpectedly been found that impure p-nitrophenol hydrolysate can be directly hydrogenated in the presence of borate ion without the formation of undesirable by-products and color and that a highly purified N-acetyl-p-aminophenol (APAP) may thereby be produced. Moreover, according to this invention boric acid is the superior acid for the reduction of nitrophenols which avoids interference of undesirable side reactions that accompany direct hydrogenation of nitrophenol hydrolysates using previous methods. The elimination of the purification step for the p-nitrophenol containing hydrolysate (i.e. from hydrolysis of p-chlorobenzene) thus providing direct hydrogenation and acetylation to produce a high purity N-acetyl-p-aminophenol (APAP) in a commercially significant development.

DESCRIPTION OF PREFERRED EMBODIMENTS

The present invention enables the use of the nitrophenol obtained directly from the hydrolysis of halonitrobenzene for the production of aminophenols by subjecting the nitrophenol to hydrogenation without prior separation and purification procedures. According to this invention, the presence of the borate ion during the reduction of the nitrophenol containing total hydrolysate from the hydrolysis of halonitrobenzenes, such as the chlorine, fluorine, or bromine derivatives, eliminates interference and side reactions caused by the presence of undesirable by-products and leading to impurities and color formation.

Another embodiment of the present invention relates to the production of N-acetyl-p-aminophenol (APAP) directly from p-nitrophenol produced by the hydrolysis of p-chloronitrobenzene without the need for extensive separation and purification procedures. It has unexpectedly been found that the presence of borate ion during reduction of p-nitrophenol permits the production of highly pure N-acetyl-p-aminophenol without laborious purification steps for the p-nitrophenol or the p-aminophenol.

Since the mechanisms involved in the hydrolysis of halobenzenes and the production of N-acetyl-p-aminophenol from chloronitrobenzene are complicated, applicant does not wish to be bound by any theory. Nevertheless, it appears that borate ion forms some complex with by-products produced in the hydrolysis of halonitrobenzenes and that the borate complex avoids undesirable side effects and discolorations that normally occur in the subsequent hydrogenation. It is, therefore, further believed that there are at least two sources for impurities and discoloration during the production of N-acetyl-p-aminophenol, i.e. one sourse arising during hydrolysis of the p-chloronitrobenzene and the other originating during hydrogenation of the p-nitrophenol.

The commercial rate to the production of N-acetyl-p-aminophenol involves the following steps:
(1) Hydrolysis of p-chloronitrobenzene to produce p-nitrophenol,
(2) Separation and purification of p-nitrophenol,
(3) Reduction of the p-nitrophenol to p-aminophenol,
(4) Separation and purification of the p-aminophenol,
(5) Acetylation of the p-aminophenol to produce N-acetyl-p-aminophenol, and
(6) Separation and purification of the N-acetyl-p-aminophenol.

As previously discussed, it has been found that if unpurified p-nitrophenol is the starting material for the reduction and acetylation, then an impure N-acetyl-p-aminophenol is produced. It would be desirable if one could proceed directly from p-chloronitrobenzene without separation and purification of the p-nitrophenol produced in the hydrolysis step.

Therefore, according to the process of the instant invention, a source of borate ion, such as boric acid may be added to the p-nitrophenol before the hydrogenation and acetylation for production of N-acetyl-p-aminophenol. Preferably, the boric acid is added to the p-chloronitrobenzene before or during the subsequent hydrolysis and the p-nitrophenol containing hydrolysate used directly in acetylation for production of highly purified APAP.

The alkaline hydrolysis of p-nitrochlorobenzene produces a suspension of sodium-p-nitrophenol in a sodium chloride solution. To insure uniformity in the composition prior to reduction, the sodium-para-nitrophenate preferably may be centrifuged and reconstituted for reduction. Nitrites produced in the hydrolysis are preferably destroyed by addition of sulfamic acid and the neutralization of the sodium salt may be accomplished by addition of sulfuric acid. Similarly the p-nitrophenol may be treated with charcoal before hydrogenation. In conventional processes, the soluble by-products remain with the p-nitrophenol solution and result in formation of undesirable reactants and color bodies if the p-nitrophenol is not further purified as by distillation or crystallization before hydrogenation and acetylation. Moreover, the use of various conventional acids during reduction, such as sulfuric, hydrochloric, phosphoric, or milder organic acids such as oxalic or acetic do not overcome the deleterious effect of direct hydrogenation of the p-nitrophenol produced as thus described. Unexpectedly it has been found that addition of borate ion in the form of boric acid or boric acid salts to the thus produced non-purified p-nitrophenol followed by reduction and acetylation overcomes the undesirable side reactions and permits production of an acceptable highly pure N-acetyl-p-aminophenol product.

The amount of borate ion used must be sufficient to complex by-products that lead to undesirable side reactions and color formation. Thus, from about 0.5 to about 20 mole percent boric acid based on p-nitrophenol may be used. Preferably, from about 10 to about 15 mole percent boric acid based on p-nitrophenol is used when proceeding from the p-chloronitrobenzene hydrolysate.

The borate ion may be introduced at different points in the APAP synthesis. For example, it may be added before, during or after the hydrolysis of the p-chloronitrobenzene. For elimination of undesirable reactions and color formation, borate ion must be present during the hydrogenation stage of the process of this invention, and to provide maximum benefit of the complexing activity. Therefore, according to this invention, conventional acid catalysts may be used when proceeding from a total hydrolysate of p-nitrophenol and will result in high purity N-acetyl-p-aminophenol only if the borate ion is also present.

The hydrogenation catalyst preferred for the reduction of the p-nitrophenol to p-aminophenol is palladium-on-carbon. Other hydrogenation catalysts may be used without affecting the overall process of this invention. For example, nickel, platinum, palladium or noble metal catalysts and their oxides may be used. During hydrogenation the temperature is preferably held below 110° C. and most preferably from about 95° C. to about 100° C. The process may be carried out at a hydrogen pressure from slightly above atmospheric pressure to several hundred atmospheres. Preferably a hydrogen pressure of from about 60 to about 80 psi is used.

After the available p-nitrophenol has been completely hydrogenated to p-aminophenol, the reaction mixture is preferably filtered to recover catalyst. The p-aminophenol may be recovered at this stage. However, according to the teaching of this invention, one may acetylate the p-aminophenol without prior separation or purification. Direct acetylation of the reduction product and minimization of undesirable side effects is possible operating preferably at a temperature of from about 60° C. to about 80° C. Thus a high purity APAP is obtained using an aqueous solvent system.

In determining purity of the N-acetyl-p-aminophenol, the caustic test and granulation test were employed. In the caustic test 100 mg. of N-acetyl-p-aminophenol is placed in a 5.0 ml. volumetric flask and diluted to volume with a 10% sodium hydroxide solution. A completely colorless solution upon the dissolution of the N-acetyl-p-aminophenol indicates acceptable pharmaceutical quality.

In the granulation test 10.0 gm. of N-acetyl-p-aminophenol (ground to 100 mesh) is placed in a 50 ml. beaker and 10.0 ml. of water is added to make a level paste. The paste is heated for 2½ hours at 50°–55° C. and then cooled to room temperature. No discoloration of the hardened mass indicates acceptable pharmaceutical grade purity. Any pink, yellow or gray discoloration indicates impure N-acetyl-p-aminophenol.

Thus, as previously described, if the N-acetyl-p-aminophenol product is discolored, it is impure. A white product or colorless product solution indicates purity, but not necessarily an acceptable purity for a pharmaceutical grade material. For a pharmaceutical grade purity, the N-acetyl-p-aminophenol product should be white and also pass the caustic test and the granulation test as set forth in the above description.

The invention is illustrated by the following examples which, however, are not to be taken as limiting in any respect.

EXAMPLE I

Boric Acid Reduction

In calculation of the crude yield of the following examples, the actual weight in grams of the recovered APAP is divided by the theoretical yield of APAP in grams. The theoretical yield is calculated by multiplying the weight in grams of the starting material (p-nitrophenol) by the ratio of the molecular weight of APAP to the molecular weight of p-nitrophenol. Similarly the weight in grams of the APAP recovered from recrystalization divided by the theoretical yield provides the recrystalized yield.

The following example shows the use of boric acid during hydrogenation of p-nitrophenol and acetylation of the p-aminophenol product:

47 lbs. of p-chloronitrobenzene in 118 lbs. of water was mixed with 50 lbs. of 50% NaOH and heated at 170°–175° C. for 3 hours to hydrolyze the p-chloronitrobenzene to p-nitrophenol.

34.9 lbs. of the total hydrolysis mixture (containing 6.5 lbs. of p-nitrophenol) was charged into a jacketed reaction vessel. Excess caustic and sodium-p-nitrophenolate was then neutralized by adding 695 g. of 50% sulfuric acid. Then, 65.5 g. (5 mole percent based on p-nitrophenol) of boric acid and 14 g. of 5% palladium-on-carbon catalyst was added. The charged vessel was purged with hydrogen, sealed, heated to a temperature of about 100° C. at 60–80 psi and maintained at 95°–100° C. throughout the hydrogenation. A total of 3576 g. of 50% sulfuric acid was fed into the reaction during hydrogenation. Hydrogenation was completed in 3 hours. The product was filtered to recover the catalyst and then the filtrate acetylated with acetic anhydride by the conventional procedure.

Quality of the APAP was much improved over reductions conducted using no boric acid and was only slightly off-color.

EXAMPLE II

Reduction of Total Hydrolysate

This comparative experiment demonstrates the necessity of boric acid for production of high quality N-acetyl-p-aminophenol beginning with total hydrolysate from p-chloronitrophenol hydrolysis:

| Acid | N-acetyl-p-aminophenol | | | |
|---|---|---|---|---|
| | Yield % | Color | Caustic Test | Granulation Test |
| $H_2SO_4$ | 86 | Off White | Fail | Poor |
| Acetic | 85 | Pink | Fail | Poor |
| $H_3PO_4$ | 83 | Gray | Fail | Poor |
| $H_2SO_4$ + Boric | 87 | White | Pass | Pass |

As can be seen from the above results, the presence of the borate ion results in a high purity colorless product without decreasing the overall product yield.

EXAMPLE III

This example demonstrates the combined boric/sulfuric acid reduction of total hydrolysate from p-chloronitrophenol.

47 lbs. of p-chloronitrobenzene in 118 lbs. of water was mixed with 50 lbs. of 50% NaOH and heated at 170°–175° C. for 3 hours to hydrolyze the p-chloronitrobenzene to p-nitrophenol.

34.9 of the total hydrolysis mixture (containing 6.5 lbs. of p-nitrophenol) was charged into a jacketed reaction vessel. Excess caustic and sodium-p-nitrophenolate was then neutralized by adding 695 g. of 50% sulfuric acid. Then, 131 g. (10 mole percent based on p-nitrophenol) of boric acid and 14 g. of 5% palladium-on-carbon catalyst was added. The charged vessel was purged with hydrogen, sealed, heated to a temperature of about 100° C. at 60–80 psi and maintained at 95°–100° C. throughout the hydrogenation. A total of 3576 g. of 50% sulfuric acid was fed into the reaction during hydrogenation. Hydrogenation was completed in 3 hours. The product was filtered to recover the catalyst and then the filtrate acetylated with acetic anhydride.

An acceptable and colorless N-acetyl-p-aminophenol solution was recovered. Upon recrystallization from 3 parts of water, a high quality white pharmaceutical grade N-acetyl-p-aminophenol was obtained at 87.2% yield.

EXAMPLE IV

This experiment relates to a large scale process and to the production of an acceptable pharmaceutical quality APAP.

A 30 gal. jacketed vessel is charged with 25.15 lbs. of p-nitrochlorobenzene, 26.8 lbs. of 50% sodium hydroxide and 63 lbs. of water. The charge is heated at 170°–175° C. for 3 hours to effect hydrolysis to p-nitrophenol. Thereafter, the charge is cooled and 18 lbs. of 50% sulfuric acid, 0.98 lbs. of boric acid (10 mole % on p-nitrophenol), and 50 g. of 5% palladium-on-carbon catalyst are added.

The mixture is heated to 100°–105° C. under a hydrogen pressure of 70 psig and 17 lbs. of 50% sulfuric acid are fed during the course of the hydrogenation. After the theoretical quantity of hydrogen is absorbed, the catalyst is filtered and the filtrate is acetylated with 17 lbs. of acetic anhydride. Thereafter, the batch is cooled and crystallized. The crystals are filtered yielding 20.7 lbs. of crude APAP corresponding to a 85.8% of the theoretical yield.

Upon one recrystallization from 43 lbs. of water containing 0.4 lbs. of sodium hydrosulfite glistening white crystals of pharmaceutical grade APAP are obtained in 92% recovery.

EXAMPLE V

The following runs demonstrate the use of boric acid as the sole acid catalyst during reduction of p-nitrophenol and the preparation of highly pure N-acetyl-p-aminophenol therefrom.

In the following runs, boric acid was added to p-nitrophenol in water and the mixture hydrogenated to completion in the presence of a palladium-on-carbon catalyst at 65°–78° C. and 68–72 psig. The p-aminophenol reaction product was filtered to recover the catalyst and then subjected to acetylation.

| Run | p-nitro-Phenol lbs. | Carbon oz. | 5% Pd on Carbon gms. | Boric Acid lbs. | Hydrogenation | | | Acetic Anhydride lbs. | Crude Yield % | Recrystal. Yield % | Caustic Test | Granulation Test |
|---|---|---|---|---|---|---|---|---|---|---|---|---|
| | | | | | Temp. °C. | PSIG | Time Hrs. | | | | | |
| A | 38 | 8 | 140 | 6 | 68–70 | 68–72 | 8.5 | 20 | — | — | Pass | Pass |
| B | 38 | 8 | 140 | 3 | 69–70 | 70–72 | 9.0 | 28 | 67 | 56 | Pass | Slt. Pink |
| C | 38 | 8 | 80 | 3 | 68–72 | 68–72 | 7.0 | 28 | 80 | 75 | Pass | Pass |
| D | 38[b] | 8 | 80 | 3 | 70 | 68–72 | 4.0 | 28 | 69 | 60 | Pass | Slt. Gray |

-continued

| Run | p-nitro-Phenol lbs. | Carbon oz. | 5% Pd on Carbon gms. | Boric Acid lbs. | Hydrogenation Temp. °C. | PSIG | Time Hrs. | Acetic Anhydride lbs. | Crude Yield % | Recrystal. Yield % | Caustic Test | Granulation Test |
|---|---|---|---|---|---|---|---|---|---|---|---|---|
| E | 38 | 8 | 80 | 3 | 68–70 | 68–70[c] | 4.0 | 28 | 91 | 80 | Pass | Pass |
| F | 38 | 8 | 80 | 3 | 65–78 | 68–72 | 4.0 | 28 | 73 | — | Pass | Pass |

[a]5% Palladium on Charcoal 50% water wet.
[b]Neutralized 55.5 lbs. of sodium p-nitrophenate to pH 1.0 with 14.5 lbs. 93% sulfuric to give the equivalent 38 lbs. p-nitrophenol.
[c]After 60% of hydrogen was absorbed, pressure was reduced to 22 PSIG to control feed rate of hydrogen.

EXAMPLE VI

Analysis of APAP Compared to Purity Standards

The following analysis compares a typical APAP product produced by the boric acid process of this invention with USP Standards:

| ANALYTICAL RESULTS | USP STANDARDS |
|---|---|
| Caustic Soln. Clear, Colorless | Report |
| Solubility Passes | To Pass |
| Melting Range 168.1–169.1° C. | 168–172° C. |
| pH 5.5 | 5.3–6.5 |
| Residue on Ignition Nil | 0.1% Max. |
| Sulfide Trace | No Trace |
| Heavy Metals Passes | 10 ppm Max. |
| 1/10 Ethanol Soln. Clear, Colorless | Clear & Colorless |
| McNeil Limits of Color 0.030 | 0.030A Max. |
| Sat. Water Soln. Colorless | Report |
| | ADDITIONAL STANDARDS |
| Granulation Satisfactory | Report |

While the invention has been described in connection with specific embodiments thereof, it will be understood that it is capable of further modifications and this application is intended to cover any variations, uses or adaptations of the invention and including such departures from the present disclosure as come within known or customary practice in the art to which this invention pertains and as may be applied to the essential features hereinbefore set forth, and as fall within the scope of the invention.

We claim:

1. An improved process for the production of aminophenol from halonitrobenzene which comprises subjecting halonitrobenzene to alkaline hydrolysis to produce nitrophenol, adding a sufficient amount of borate ion to interact with undesirable by-products of said alkaline hydrolysis, completely reducing the nitrophenol product containing said borate ion in the presence of a metal hydrogenation catalyst to convert available nitrophenol to aminophenol, and recovering said aminophenol.

2. The process of claim 1 wherein the amount of borate ion present is from about 0.5 to about 20 mole percent based on nitrophenol.

3. The process of claim 2 wherein the amount of borate ion is from about 10 to about 15 mole percent based on nitrophenol.

4. The process of claim 1 wherein hydrogenation is conducted in the presence of a metal hydrogenation catalyst.

5. The process of claim 4 wherein said catalyst is palladium.

6. The process of claim 5 wherein said catalyst is palladium-on-carbon.

7. The process of claim 1 wherein the temperature during hydrogenation is maintained below about 110° C.

8. The process of claim 7 wherein the temperature is maintained from about 95° C. to about 100° C.

9. The process of claim 1 wherein the halonitrobenzene is p-chloronitrobenzene.

10. The process of claim 1 wherein the nitrophenol is p-nitrophenol.

11. An improved process for the production of N-acetyl-p-aminophenol from p-chloronitrobenzene which comprises subjecting p-chloronitrobenzene to alkaline hydrolysis to produce p-nitrophenol, adding a sufficient amount of borate ion to interact with undesirable by-products of said alkaline hydrolysis, completely reducing the p-nitrophenol hydrolysis product containing said borate ion in the presence of a metal hydrogenation catalyst to convert available p-nitrophenol to p-aminophenol, acetylating the p-aminophenol to N-acetyl-p-aminophenol, and recovering N-acetyl-p-aminophenol.

12. The process of claim 11 wherein the amount of borate ion present is from about 0.5 to about 20 mole percent based on p-nitrophenol.

13. The process of claim 12 wherein the amount of borate ion is from about 10 to about 15 mole percent based on p-nitrophenol.

14. The process of claim 11 wherein hydrogenation is conducted in the presence of a metal hydrogenation catalyst.

15. The process of claim 14 wherein said catalyst is palladium.

16. The process of claim 15 wherein said catalyst is palladium-on-carbon.

17. The process of claim 11 wherein the temperature during hydrogenation is maintained below about 110° C. during hydrogenation.

18. The process of claim 17 wherein the temperature is maintained from about 95° C. to about 100° C.

19. The process of claim 11 wherein a strong acid is present in the hydrogenation step.

20. The process of claim 19 wherein the strong acid is sulfuric acid.

21. An improved process for the production of N-acetyl-p-aminophenol from p-chloronitrobenzene which comprises subjecting p-chloronitrobenzene to alkaline hydrolysis to produce p-nitrophenol, adding a sufficient amount of borate ion to interact with undesirable by-products of said alkaline hydrolysis, completely reducing the p-nitrophenol hydrolysis product containing said borate ion in the presence of a palladium catalyst to convert available p-nitrophenol to p-aminophenol, acetylating the p-aminophenol to N-acetyl-p-aminophenol, and recovering N-acetyl-p-aminophenol.

* * * * *